United States Patent [19]

Boschelli et al.

[11] Patent Number: 5,434,188
[45] Date of Patent: Jul. 18, 1995

[54] 1-ETHER AND 1-THIOETHER-NAPHTHALENE-2-CARBOXAMIDES AS INHIBITORS OF CELL ADHESION AND AS INHIBITORS OF THE ACTIVATION OF HIV

[75] Inventors: Diane H. Boschelli, Plymouth; David T. Connor, Ann Arbor; Sony S. Khatana, Northville, all of Mich.; James B. Kramer, Sylvania, Ohio; Paul C. Unangst, Ann Arbor, Mich.

[73] Assignee: Warner-Lambert Company, Morris Plains, N.J.

[21] Appl. No.: 207,323

[22] Filed: Mar. 7, 1994

[51] Int. Cl.⁶ .................. A61K 31/165; C07C 233/65
[52] U.S. Cl. .................................... 514/617; 514/618; 514/519; 514/620; 514/886; 564/161; 564/162; 564/163; 564/164; 564/165; 564/166; 564/167; 564/170; 564/171; 564/172; 564/173
[58] Field of Search ........ 564/162, 172, 173, 163–166, 564/167, 170, 171; 514/617, 618, 619, 622, 886

[56] References Cited

U.S. PATENT DOCUMENTS

| | | | |
|---|---|---|---|
| 1,935,930 | 11/1933 | Zitscher et al. | 564/173 |
| 4,767,776 | 8/1988 | Connor et al. | 514/381 |

FOREIGN PATENT DOCUMENTS

| | | | |
|---|---|---|---|
| 1303455 | 8/1962 | France | 564/173 |
| 50089352 | 7/1975 | Japan | 564/172 |
| 1085437 | 10/1967 | United Kingdom | 564/173 |
| 2038808 | 7/1980 | United Kingdom | 564/173 |

OTHER PUBLICATIONS

M. A. Jutila, et al., *Transplantation*, 48, 1989, 727–731.
A. Wardlaw, *Clin & Exper Allergy*, 20, 1990, 619–626.
R. P. McEver, *Thrombosis & Hemostasis*, 65(3), 1991, 223–228.
T. A. Springer, *Nature*, 346, 1990, 425–434.
M. Hiroaki, et al., *Proc Natl Acad Sci USA*, 83:1986, 191–1915.
B. C. Hakkert, et al., *Blood*, vol. 78, No. 10, 1991, 2721–2726.
J. Pober, et al., *J. Ummun*, 137, No. 6, 1986, 1893–1896.
C. W. Smith, et al., *J Clin Invest*, 82, 1988, 1746–1756.
M. P. Bevilacqua, et al., *Proc Natl Acad Sci, USA*, 84, 1987, 9238.
M. A. Vadas, *Biochemical Pharm*, 40(8), 1990, 1683–1687 et al.

*Primary Examiner*—Shailendra Kumar
*Attorney, Agent, or Firm*—Charles W. Ashbrook

[57] ABSTRACT

1-Ether and 1-thioether-naphthalene-2-carboxamides are described, methods of manufacture therefor and their use as agents which inhibit leukocyte adherence to vascular endothelium and, as such, are effective therapeutic agents for treating inflammatory diseases, and their utility in inhibiting the activation of human immunodeficiency virus (HIV), latent in infected humans.

11 Claims, No Drawings

1-ETHER AND 1-THIOETHER-NAPHTHALENE-2-CARBOXAMIDES AS INHIBITORS OF CELL ADHESION AND AS INHIBITORS OF THE ACTIVATION OF HIV

BACKGROUND OF THE INVENTION

The present invention is for novel 1-ether and 1-thioether-naphthalene-2-carboxamides and pharmaceutically acceptable acid addition salts thereof and their use to prevent the adhesion of leukocytes to endothelial cells. (HIV) Leukocyte adherence to vascular endothelium is integral to the pathogenesis of inflammation. The adhesion process precedes transendothelial migration of leukocytes into surrounding tissue and ensuing tissue damage. Compounds that can block this initial adhesive interaction are expected to have efficacy in the treatment of inflammatory diseases such as rheumatoid arthritis, osteoarthritis, asthma, and psoriasis. Other indications would include but are not limited to adult respiratory distress syndrome, reperfusion injury, ischemia, ulcerative colitis, vasculidites, atherosclerosis, inflammatory bowel disease and tumor metastases.

Adhesion receptors are organized into three main families: the selectins, the immunoglobulin superfamily, and the integrins (Nature, 345:426 (1990)). Members of all three classes are involved in mediating leukocyte adhesion during inflammation (for reviews of this area see: Thrombosis and Hemostasis, 65(3):223 (1991), Clinical and Experimental Allergy, 20:619 (1990), Transplantation, 48:727 (1989), Biochemical Pharm., 40(8):1683 (1990)). Endothelial leukocyte adhesion molecule-1 (ELAM-1 or E-selectin) is a member of the selectin family of glycoproteins that promote cell-cell adhesion. E-selectin is reported to be maximally expressed on the surface of endothelial cells 4 hours after stimulation of the endothelial cells with cytokines, such as interleukin-1 (IL-1) or tumor necrosis factor α (TNF-α) or other inflammatory mediators, such as lipopolysaccharide (LPS) (Pro. Nat. Acad. Sci., 84:9238 (1987)).

Intercellular adhesion molecule-1 (ICAM-1) is a member of the immunoglobulin superfamily. It is also regulated with maximum expression occurring 12–24 h after stimulus. It has been shown that 4 hours after the endothelial cells are stimulated with an inflammatory mediator both E-selectin and ICAM-1 are present on the cell surface (J. Clin. Invest., 82:1746 (1988) and J. Immune., 137:1893 (1986), Blood, 78:2721 (1991)).

The 1-ether and 1-thioether-naphthalene-2-carboxamides of the present invention have been shown to inhibit the adhesion of neutrophils to human umbilical vein endothelial cells (HUVECS) stimulated with TNFα in an in vitro assay.

The present invention also relates to the novel ethers and thioethers of naphthalene-2-carboxamides for treating humans infected with human immunodeficiency virus (HIV) by inhibiting the activation of HIV, latent in infected humans.

The pathogenesis of the human immunodeficiency virus (HIV) is complicated and as of yet not completely understood. The virus life cycle has theoretically been divided into afferent and efferent components. Virus binding, fusion, reverse transcription, and finally integration are among those events which encompass the afferent component of the life cycle. It is the afferent component of the HIV life cycle which is responsible for primary infection of HIV in an individual, generally followed by a burst of viraemia with or without clinical symptoms.

Many therapeutic strategies have been developed and targeted for intervention during the afferent events. See for example, Mitsuya H, Broder S, "Inhibition of the In Vitro Infectivity and Cytopathic Effect on Human T-lymphotropic Virus Type III/lymphadenopathy Virus-associated Virus (HTLV-III/LAV) by 2′,3′-Dideoxynocleosides," Proc. Natl. Acad. Sci. (USA) 83:1911–1915 (1986).

Whereas different stages of the afferent component offer the potential for effective therapeutic intervention, it has become increasingly apparent that intervention solely at these points is insufficient. After becoming infected with HIV and the disease progresses through the afferent stages, an individual experiences a prolonged period of clinical latency which may extend for several years and the individual remains in good health. At this point in time, low to absent levels of viraemia and virus replication in peripheral-blood cells are achieved. At a later point, however, the disease eventually progresses to life-threatening immunosuppression (AIDS) for which there remains no cure. These later events are the clinical manifestations of the efferent stages of HIV infection.

The efferent component of the HIV life cycle includes those events necessary for the HIV provirus to successfully transcribe, translate, assemble, and produce virions. Onset of the events necessary for HIV-infected cells to progress from an asymptomatic, non-HIV expressive stage to a symptomatic, HIV expressive stage is referred to as activation. Presently, the efferent component and the cellular basis for activation is not completely understood. Nevertheless, if novel therapeutic agents and strategies are developed and implemented during the clinically asymptomatic phase to fight the progression toward AIDS, some hope may be afforded the estimated one million infected, but clinically latent, individuals.

SUMMARY OF THE INVENTION

Accordingly, the present invention is of a compound of the formula (I) or a pharmaceutically acceptable acid addition salt thereof.

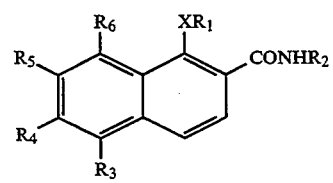

wherein
$R_1$ is lower alkyl, phenyl or benzyl;
$R_2$ is hydrogen or lower alkyl;
X is O or $S(O)_n$;
n is an integer of 0, 1 or 2, and
$R_3$, $R_4$, $R_5$, $R_6$ are each independently hydrogen, hydroxy, halogen, trifluoromethyl, lower alkyl, lower alkoxy, phenoxy, benzyloxy, nitro, or —$NR_7R_8$, in which $R_7$ and $R_8$ are each independently hydrogen or lower alkyl; with the proviso that either $R_4$ or $R_5$ must be lower alkoxy.

The present invention includes pharmaceutical compositions comprising a therapeutically effective amount of a compound of the Formula I above together with a pharmaceutically acceptable carrier.

A third aspect of the present invention is a method of treating diseases mediated by inhibiting the adhesion of leukocytes to endothelial cells comprising administering to a host in need thereof a pharmaceutical composition containing a compound of Formula I in unit dosage form.

A fourth aspect of the present invention is a method of treating a mammal infected with HIV, which comprises administering to said mammal a pharmaceutical composition containing a compound of Formula I in unit dosage form.

DETAILED DESCRIPTION

The terms used in defining the compounds of Formula I of the present invention are defined as follows.

Lower alkyl and lower alkoxy mean a straight or branched alkyl or alkoxy group having 1 to 4 carbon atoms and includes, for example, methyl, ethyl, propyl, i-propyl, or otherwise referred to as (methyl)ethyl, and t-butyl, or otherwise referred to as 1,1-(dimethyl)-ethyl, and correspondingly, for example, methoxy, ethoxy, i-propoxy, or otherwise referred to as 1-(methyl)ethoxy and the like.

Halogen includes fluorine, chlorine, bromine, or iodine.

The compounds of the Formula I are capable of further forming pharmaceutically acceptable acid addition salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkoanoic acids, hydroxy, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glutamine (see, for example, Berge SM, et al., "Pharmaceutical Salts," *Journal of Pharmaceutical Science* 66:1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

A preferred embodiment of the present invention is a compound of Formula I defined above, wherein $R_3$ and $R_6$ are hydrogen and at least one of $R_4$ and $R_5$ is lower alkoxy.

A more preferred embodiment of the present invention is a compound of Formula I defined above, wherein $R_3$ and $R_6$ are hydrogen, at least one of $R_4$ and $R_5$ is lower alkoxy and the other is hydrogen; X is O, and $R_1$ is lower alkyl.

Particularly valuable are:

7-methoxy-1-(1-methylethoxy)-2-naphthalenecarboxamide,

N-ethyl-7-methoxy-1-(1-methylethoxy)-2-naphthalenecarboxamide, 7-methoxy-1-(1-methylethoxy-N-(1-methylethyl)-2-naphthalenecarboxamide, 1,7-bis-(1-methylethoxy)-2-naphthalenecarboxamide, 6-methoxy-1-(1-methylethoxy)-2-naphthalenecarboxamide, 1,7-dimethoxy-2-naphthalenecarboxamide.

In determining when a cell adhesion inhibitor or inhibitor of HIV activation is indicated, of course inter alia, the particular condition in question and its severity, as well as the age, sex, weight, and the like of the subject to be treated, must be taken into consideration and this determination is within the skill of the attendant physician.

For medical use, the amount required of a compound of Formula I or a pharmacologically acceptable salt thereof to achieve a therapeutic effect will, of course, vary both with the particular compound, the route of administration, the mammal under treatment, and the particular disorder of disease concerned. A suitable dose of a compound of Formula I or a pharmacologically acceptable salt thereof for a mammal suffering from, or likely to suffer from any condition as described hereinbefore is 0.1 µg to 500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range 0.1 ng to 100 µg of the compound per kilogram, typically about 0.1 µg/kg.

In the case of oral dosing for the treatment or prophylaxis of arthritis or inflammation in general, due to any course, a suitable dose of a compound of Formulas I or a physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example, from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of Formula I or a pharmacologically acceptable acid addition thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations know in the art.

The formulations may conveniently be presented in unit dosage form and may be prepared by any of the methods well known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention, particularly those of Formula I, as inhibitors of leukocyte adherence to vascular endothelium and thus in treating inflammatory-related diseases or conditions may be demonstrated by their effectiveness in various standard test procedures. A description of each procedure and exemplary test results follows.

METHOD FOR DETERMINING THE INHIBITION OF HUMAN NEUTROPHIL ADHESION TO TNF-α, IL-α, AND LPS-STIMULATED HUMAN UMBILICAL VEIN ENDOTHELIAL CELLS (ECA)

Isolation of Neutrophils

Neutrophils were isolated from anticoagulant-treated venous blood obtained from healthy human volunteers according to the method of Ferrante and Thong (*J. Immunol. Methods* 24:389-393 (1978)). The cell preparations consisted of greater than 98% neutrophils.

Endothelial Cell Culture

Second passage human umbilical vein endothelial cells (HUVEC) (Clonetics, San Diego, Calif.) were seeded into Falcon 24-well cell culture plates (Becton Dickinson, Lincoln Park, N.J.) at approximately $2 \times 10^4$ cells per well. The cells were grown to confluent monolayers in endothelial basal medium (EBM, Clonetics) supplemented with 5% fetal calf serum (Hyclone Laboratories, Logan, Utah), 10 ng/mL EGF, 1 μg/mL hydrocortisone, 0.4% bovine brain extract (Clonetics) in 5% $CO_2$ at 37° C.

Neutrophil Adhesion

Neutrophils ($30 \times 10^6$) were labeled for 60 minutes at 37° C. with 100 μCi $Na^{51}CrO_4$ (ICN Biomedicals, Costa Mesa, Calif.) in 2.0 mL $Ca^{2+}-$ and $Mg^{2+}-$ free Hanks' balanced salt solution (HBSS, GIBCO Laboratories, Grand Island, N.Y.). The cells were washed two times in HBSS and suspended in unsupplemented EBM.

Stimulation of HUVEC with tumor necrosis factor-α (TNF-α) (Genzyme, Cambridge, Mass.), interleukin (IL-1α) (Genzyme) or *E. coli* 0111:B4 lipopolysaccharide (LPS) (Sigma) in the presence or absence of drug was initiated 4 hours prior to the addition of neutrophils. The suspension medium was unsupplemented EBM or supplemented EBM for studies with cytokines or LPS, respectively. Such treatment has been shown to promote maximal expression of the endothelial cell-leukocyte adhesion molecule ELAM-1 as well as expression of ICAM-1 (*J. Immunol.* 137:1893 (1986); *Proc. Natl. Acad. Sci. USA* 9238 (1987)). Immediately prior to addition of $^{51}Cr$-labeled neutrophils to the HUVEC monolayers, the cultures were washed with 1 mL unsupplemented media to remove stimulus and/or drug. Neutrophils ($5 \times 10^5$) were then added to the HUVEC in 0.5 mL unsupplemented media and incubated at 37° C. for 30 minutes. Nonadherent neutrophils were removed by aspiration. Following an additional wash, adherent neutrophils were lysed with 0.5 mL 1N $NH_4OH$ overnight at 37° C. Lysates were collected and the radioactivity in each well was determined by gamma ray spectroscopy. An alternate method for determining adhesion is also used and described as follows.

MODIFIED METHOD FOR DETERMINING THE INHIBITION OF HUMAN NEUTROPHIL ADHESION TO TNF-α STIMULATED HUMAN UMBILICAL VEIN ENDOTHELIAL CELLS

Cell Culture

Second passage HUVEC (Clonetics Corporation, San Diego, Calif., CC-2617) were seeded into Corning (Corning glass works, Corning, N.Y.) 96-well cell culture plates at approximately $5 \times 10^3$ cells/well and grown to confluency in supplemented endothelial basal medium (EBM, MCDB-131, Clonetics, 10 ng/mL EGF, 1 μg/mL hydrocortisone, 0.4% bovine brain extract, 5% Fetal Bovine Serum). One day prior to running the assay, typically 3 days postseeding, the cultures were re-fed with 0.2 mL/well supplemented EBM (S-EBM).

Preparation of Test Compounds

Test compounds were prepared as 10 mL stock solutions at a concentration of 1.0 mM. The compound were initially solubilized in 0.1 mL DMSO followed by the addition of 9.9 mL S-EBM. The drug preparations were then diluted in one step to a concentration of 66.6 μM. Solubilizations and dilutions were performed in polystyrene containers.

Stimulation of HUVEC

Recombinant human tumor necrosis factor-α(TNF, Genzyme, Boston, Mass., code TNF-H) was prepared at 400 U/mL in S-EBM. Stock TNF was prepared to 20,000 U/mL in Delbecco's phosphate buffered saline (PBS, Gibco, Grand Island, N.Y.) plus 0.1% BSA and stored at −70° C. HUVEC were washed one time with 0.2 mL warm unsupplemented EBM and then stimulated for 4 hours at 37° C. with 200 U/mL TNF in the presence of 33.3 μM test compound. This was accomplished by adding 0.1 mL of 400 U/mL TNF and 0.1 mL 66.6 μM test compound. These additions were done slowly as to not disrupt the HUVEC monolayer. Each compound was tested in six wells. Unstimulated (Vehicle control) and TNF-stimulated without test compound treatments were also run in each plate.

Labeling of Neutrophils

One hour prior to adding the neutrophils to the HUVEC, neutrophils ($5 \times 10^6$/mL) were labeled for 30 minutes at 37° C. with 5 μM calcein-AM (Molecular Probes, Eugene, Oreg.) in Hanks' balanced salt solution plus 0.45% BSA. Stock calcein was prepared to 5 mM in anhydrous DMSO and stored desiccated at $-20°$ C. At the end of the incubation the cells were washed two times in cold HBSS and resuspended to a final concentration of $1 \times 10^6$ cells/mL in unsupplemented EBM.

Addition of Neutrophils to HUVEC

At the end of the 4-hour stimulation and immediately prior to the addition of the neutrophils to the HUVEC monolayer, the plates were washed with 0.2 mL warm unsupplemented EBM to remove TNF and drug. Neutrophils ($1 \times 10^5$ cells) were slowly added to each of the treated wells and incubated for 30 minutes at 37° C. At the end of the incubation the plates were washed two times with 0.2 mL warm unsupplemented EBM followed by a final addition of 0.1 mL for plate scanning.

Determination of Relative Fluorescence

The relative fluorescence was determined using a Millipore Cytofluor 2300 system (excitation=480, emission=530, sensitivity=4).

means of the inhibition values were used to determine the $IC_{50}$.

The ELISA

Murine monoclonal anti-human ICAM-1 (R & D Systems, Cat No. BBA-4) or murine monoclonal anti-human E-selectin (R & D, Cat No. BBA-2) dissolved in DMEM/2%BSA were added to each well at 0.5 μg/mL and allowed to incubate at 37° C. for 2 hours. HUVEC monocultures were then washed 4 times with DMEM/2%BSA. A peroxidase conjugated sheep anti-mouse IgG (Cappel) was added (1:3,000 dilution) and allowed to incubate 1 hour at 37° C. The cells were then washed 4 times with DMEM. A color reagent (Biorad) was added to the fixed cells and incubated 15 minutes at room temperature. The reaction was stopped with a 2% oxalic acid solution and the absorbance read at 414 nm on a titertek plate reader.

Compound Testing

Compounds were dissolved in DMSO at a concentration of 30 mmol and diluted with media to obtain final testing concentrations. HUVECs received compound dissolved in media 30 minutes before the TNFα challenge. The absorbance of non-stimulated HUVECs was subtracted from the absorbance values of TNFα stimulated cells before percent inhibition was determined. Percent inhibition was determined by comparing the absorbance of vehicle treated cells with drug treated cells. $IC_{50}$s were determined using linear regression analysis.

The results obtained with certain compounds of the present invention are shown in Table I.

TABLE I

| Example | R$_4$, R$_5$ | R$_1$ | R$_2$ | ECA % Inhib or IC$_{50}$ μM | ICAM/ESEL % Inhib @ 30 μM | OM-10n (IC$_{50}$ μM) |
|---|---|---|---|---|---|---|
| 1 | H—OMe | i-Pr | H | 11$^a$ | 77%/84% | 2.5 |
| 2 | H—OMe | i-Pr | Et | 73%$^d$ | | |
| 3 | H—OMe | i-Pr | i-Pr | 64%$^c$ | | |
| 4 | H—OMe | i-Pr | Bn | 14%$^d$ | | |
| 5 | H, OiPr | i-Pr | H | 45%$^b$ | | 0.5 |
| 6 | OMe, H | i-Pr | H | 9%$^c$ | | |
| 7 | H—OMe | Me | H | 15%$^c$ | | |

$^a$IC$_{50}$ μM
$^b$% Inhibition at 100 μM; neutrophils labeled with Cr
$^c$% Inhibition at 33 μM; neutrophils labeled with calcein
$^d$% Inhibition at 100 μM; neutrophils labeled with calcein Calculations The assay was considered valid if the TNF-stimulation of the HUVEC resulted in a 300% increase in neutrophil adherence over adherence to unstimulated HUVEC. Results were expressed as means of percent inhibition of TNF-stimulated adherence, using the following equation:

$$\% \text{ Inhibition} = 100 - \left[ \frac{\text{stimulated adherence}_{(drug)} - \text{unstimulated adherence}}{\text{stimulated adherence}_{(control)} - \text{unstimulated adherence}} \right] \times 100$$

Some of these compounds were tested at concentrations of 33.3 μM, 10.0 μM, 3.3 μM, and 1.0 μM to determine IC$_{50}$ values. Linear regression analysis of the The compounds of the present invention, particularly of Formula I, have been found to inhibit the activation of the human immunodeficiency virus (HIV), latent in infected mammals, and therefore are useful in the treatment of AIDS.

Attempts at understanding the virologic and cellular basis for the clinical asymptomatic period reveal that HIV exists as a dormant or nonexpressing provirus in a reservoir population of chronically infected cells. A specific type of HIV, HIV-1, has been the subject of a number of different research projects which have shown that the virus exists as a dormant or nonexpressing provirus in a reservoir population of chronically infected T-lymphocytic cells. Greater detail concerning the nuclear and biochemical mechanism responsible for maintaining the nonexpressive viral state, however, is beyond the scope of this review, but can be found in detail elsewhere. Mechanisms of HIV-1 Latency, Bednarik, et al., *AIDS* 6:3-16 (1992).

Until recently, it was believed that HIV was dormant or nonexpressing in all the reservoir population of chronically infected cells during the clinical asymptomatic period. Observations of the low to absent levels of viraemia and virus replication in peripheral blood cells led to the impression that HIV disease was not active during the clinical asymptomatic period. A team of scientists, however, have discovered that a true state of microbiological latency does not exist during the course of HIV infection. Fauci AS, et al., HIV Infection is Active and Progressive in Lymphoid Tissue During the Clinically Latent Sate of Disease, *Nature* 362:355-358 (1993).

The scientists reported a dichotomy between the levels of viral burden and virus replication in peripheral blood versus lymphoid organs during clinical latency. Based on these findings, therefore, the scientist have discovered that "peripheral blood does not accurately reflect the actual state of HIV disease, particularly early in the clinical course of HIV infection. In fact, HIV disease is active and progressive even when there is little evidence of disease activity by readily measured viral parameters in the peripheral blood, and the patient is experiencing clinical latency."

Inevitably, the disease state of HIV progresses from the clinically latent asymptomatic period to the expressive and active symptomatic period. Through the use of several different models, an understanding of the cellular pathways involved in HIV activation from laboratory latency has begun to unfold. According to Butera, et al., *AIDS* 6;994 (1992), many of the cellular models of latency can be induced to express HIV-1 upon treatment with cytokines. This indicates that in the state of microbiologic latency, HIV-1 awaits an extracellular stimulus before initiating replication. This signal not only can be mediated through a soluble cytokine interaction with its receptor, but also through receptor-receptor interactions which occur during cell to cell communication or cellular stress such as UV light exposure and heat shock. Furthermore, an extracellular induction signal can be generated in an autocrine or paracrine fashion so that an HIV-1 activated cell can propagate its own expression while activating a nearby latent cell.

Additional factors have been considered by those of skill in the art to be involved in the activation of HIV. One study has shown that 12-0-tetradecanoylphorbol-13-acetate (TPA) mediates CD4 down regulation and viral expression in HIV-infected cells. Hamamoto, et al., *Biochem. Biophys. Res. Commun.* 164:339-344 (1989). Interestingly, Hamamoto also examined the effect of the potent protein kinase C inhibitors staurosporine, H-7, and UCN-01 on TPA-mediated CD4 down regulation and augmentation of HIV expression. Staurosporine was found to be an effective TPA inhibitor for both of these actions.

The cellular pathways involved in mediating the activating signal from the plasma membrane to the integrated virus, resulting in HIV-1 expression, are much less clear. Recently, the development of a reliable and simple system for evaluating compounds that could prevent activation of latent HIV was reported at the National Cooperative Discovery Grant (NCDDG)/AIDS by P. Feorino, S. T. Butera, T. M. Folks, and R. F. Schinazi, Nov. 3-7, 1991. The assay system employed the OM-10.1 cell line, a unique chronically-infected promyelocytic clone which remains CD4+ until HIV-1 activation with tumor necrosis factor-α. The expression of CD4+ on the cell surface and the activity of reverse transcriptase are used as markers for quantitating viral expression. Alternatively, other HIV markers, such as protease activity, which are known to those of skill in the art can be used. OM-10.1 cells remain CD4+ until viral activation and respond to tumor necrosis factor induction, and therefore, these cultures are used to conveniently and rapidly examine pharmacologics for an ability to prevent CD4+ to prevent CD4+ down modulation (decrease in expression of CD4+ on the cell surface) and HIV-1 expression.

A variety of compounds known to have antiviral properties against either acutely or chronically infected cells were evaluated for their ability to inhibit HIV expression in these OM-10.1 cells. Several compounds that interact with biochemical pathways that may interfere with the reactivation process were also examined. The results of the evaluation were presented in a poster at the NCDDG/AIDS, San Diego, Calif., Nov. 3-7 (1991). Among some 48 compounds evaluated, 3'-fluoro-3'-deoxythymidine (FLT), interferon Y, and desferrioxamine were considered modest inhibitors of the activation of HIV-1.

A representative compound of Formula I, 7-methoxy-1-(1-methylethoxy)-2-naphthalenecarboxamide showed an $IC_{50}$ of 2.5 $\mu$M inhibition in OM-10.1 cells.

The compounds of the present invention may be prepared by the following methods. The general approach requires as starting materials the 1-hydroxy-2-naphthalene esters of structure 1 (Scheme 1) prepared as previously documented [Connor D. T., et al., *J. Med. Chem*, 35:958 (1992) and Connor D. T., et al., U.S. Pat. No. 4,767,776 which patent is incorporated herein by reference]. The conversion of compounds of type 1 to those of this invention, where X is oxygen is shown in scheme 1. The esters are treated with an alkyl or aryl halide in the presence of a base such as potassium t-butoxide or sodium hydride in tetrahydrofuran, acetonitrile, or dimethylsulfoxide at 0°-80° C. to provide esters of type 2. Hydrolysis of the ester to the acid 3 followed by conversion to either the acid chloride with a reagent such as oxalyl chloride or to a leaving group such as an imidazolide by treatment with N,N-carbonyldiimidazole and subsequent reaction with an alcohol or phenol provides 4. Alternatively 2 can be treated with an amine under high pressure or with lithium amide in anhydrous ammonia to provide compounds of structure 4. Another approach is reaction of 1 with an amine to give an amide of type 5, followed by alkylation to give 4.

Those compounds of the invention where X is sulfur are prepared from the corresponding 1-thiol-2-naphthalene esters (scheme 2). Starting with the 1-hydroxy compounds 1, reaction with dimethylthiocarbamoyl chloride in the presence of a base such as DBU in a solvent such as DMF provides the dimethylaminothioxomethoxy compounds of structure 6. Heating 6 at high temperatures in a solvent such as diphenyl ether yields the dimethylaminocarbonylthio analogs 7. Hydrolysis with a base such as sodium hydroxide in a solvent such as aqueous methanol provides the 1-thio-2-naphthalenecarboxlic acid. Esterification with diazomethane or with a strong acid such as sulfuric acid in methanol provides the methyl ester 8. Those reactions depicted in scheme 1 can be applied to 8 to prepare compounds of type 9. Treatment of compounds of type 9 with an oxidizing agent such as m-chloroperbenzoic acid (m-CPBA) or sodium perborate provides compounds of type 10 where n is 1 or 2; with the extent of oxidation depending upon the reagent used and the conditions employed, i.e. temperature and time.

The routes depicted here are not exclusive. Conditions within the description of scheme 1 through 2 and variations in the description are known or can readily be determined from analogous reactions known to one skilled in the art.

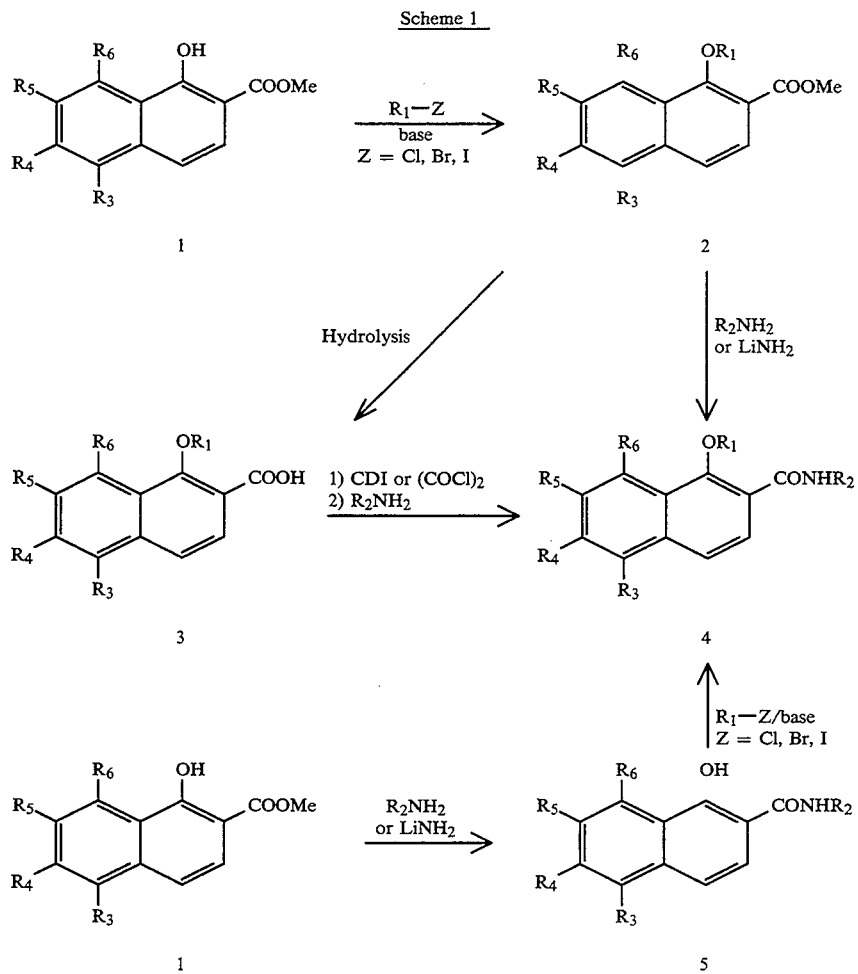

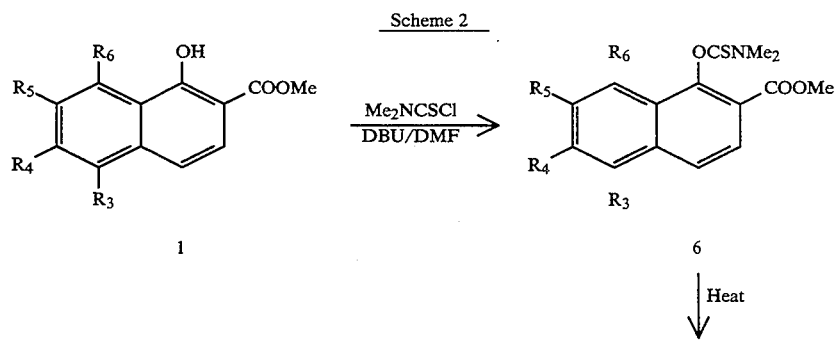

Scheme 2

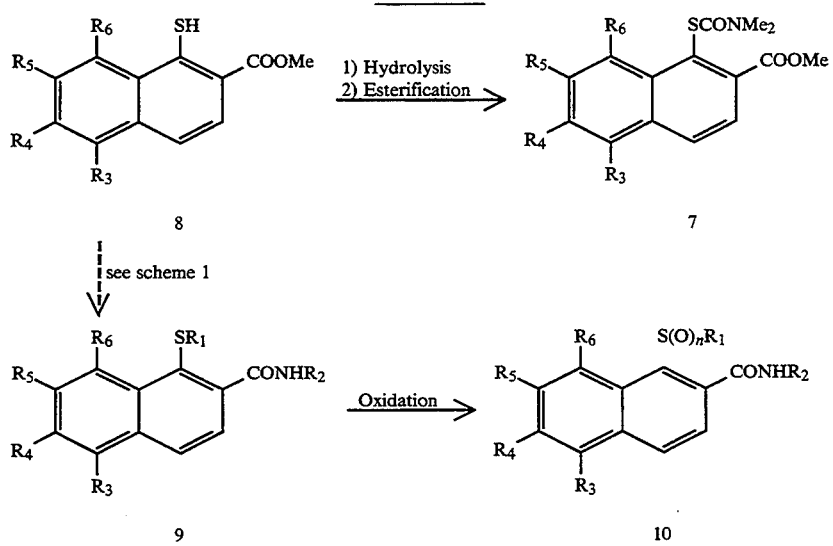

The following examples are illustrative of the preparation of the compounds of the present invention.

For the preparation of all the 1-alkoxy-2-naphthalenecarboxylic acids used as starting materials see: Connor D. T, et al, U.S. Pat. No. 4,767,776.

EXAMPLE 1

7-Methoxy-1-(1-methylethoxy)-2-naphthalenecarboxamide

To a room temperature solution of 7-methoxy-1-(1-methylethoxy)-2-naphthalenecarboxylic acid (141 mg, 0.54 mmol) in 10 mL of THF is added N,N-carbonyldiimidazole (105 mg, 0.65 mmol). The solution is heated at reflux for 1 hour and cooled slightly. Aqueous $NH_4OH$ (2.5 mL) is added and the reaction mixture is stirred at room temperature for 40 minutes then partitioned between 1:1 hexane:ethyl acetate and brine. The organic layer is dried over $MgSO_4$, filtered, and concentrated in vacuo. The crude product is recrystallized from hexane and ethyl acetate to provide 7-methoxy-1-(1 methylethoxy)-2-naphthalenecarboxamide in 68% yield; mp 172°-174° C.

EXAMPLE 2

N-Ethyl-7-methoxy-1-(1-methylethoxy)-2-naphthalenecarboxamide

To a room temperature solution of 7-methoxy-1-(1-methylethoxy)-2-naphthalenecarboxylic acid (200 mg, 0.77 mmol in 5 mL of THF is added N,N-carbonyldiimidazole (162 mg, 1.00 mmol). The solution is heated at reflux for 1 hour and cooled slightly. Ethylamine (0.44 mL of a 70% aqueous solution) is added and the reaction mixture is stirred at room temperature for 30 minutes, followed by partitioning between ethyl acetate, and brine. The organic layer is dried over $MgSO_4$, filtered, and concentrated in vacuo. The crude product is chromatographed on silica gel eluting with hexane:ethyl acetate (2:1) to provide N-ethyl-7-methoxy-1-(1-methylethoxy)-2-naphthalenecarboxamide in 70% yield; mp 78°-79° C.

EXAMPLE 3

7-Methoxy-1-(1-methylethoxy)-N-(1-methylethyl)-2-naphthalenecarboxamide

To a room temperature solution of 7-methoxy-1-(1-methylethoxy)-2-naphthalenecarboxylic acid (200 0.77 mmol) in 5 mL of THF is added oxalyl chloride (0.08 mL, 0.92 mmol) followed by DMF (0.015 mL). The solution is stirred at room temperature for 2 hours. Isopropylamine (0.39 mL) is added and the reaction mixture is stirred at room temperature overnight. The reaction mixture is diluted with ethyl acetate and washed with 1N HCl, saturated $NaHCO_3$, and brine. The organic layer is dried over $MgSO_4$, filtered, and concentrated in vacuo. The crude product is chromatographed on silica gel eluting with hexane:ethyl acetate (2:1) to provide 7-methoxy-1-(1-methylethoxy)-N-(1-methylethyl)-2-naphthalenecarboxamide in 72% yield; mp 62°-64° C.

EXAMPLE 4

7-Methoxy-1-(1-methylethoxy)-N-(phenylmethyl)-2-naphthalenecarboxamide

To a room temperature solution of 7-methoxy-1-(1-methylethoxy)-2-naphthalenecarboxylic acid (200 mg, 0.77 mmol) in 5 mL of THF is added N,N-carbonyldiimidazole (162 mg, 1.00 mmol). The solution is heated at reflux for 1 hour and cooled slightly. Benzylamine (0.50 mn) is added and the reaction mixture is stirred at room temperature overnight. The mixture is diluted with ethyl acetate and washed with brine. The organic layer is dried over $MgSO_4$, filtered, and concentrated in vacuo. The crude product is chromatographed on silica gel eluting with hexane:ethyl acetate (2:1) to provide 7-methoxy-1-(1-methylethoxy)-N-(phenylmethyl)-2-naphthalene-carboxamide in 73% yield; mp 88°-90° C.

EXAMPLE 5

1,7-Bis-(1-methylethoxy)-2-naphthalenecarboxamide

To a room temperature solution of 1,7-bis-(1-methylethoxy)-2-naphthalenecarboxylic acid (200 mg, 0.69 mmol) in 10 mL of THF is added N,N-carbonyldiimidazole (135 mg, 0.83 mmol). The solution is heated at reflux for 1 hour and cooled to room temperature. Aqueous $NH_4OH$ (4 mL) is added and the reaction mixture is stirred at room temperature for 30 minutes, then poured into ethyl acetate, and washed with aqueous $NaHCO_3$ and brine. The organic layer is dried over MgSO₄, filtered, and concentrated in vacuo. The crude product is recrystallized from methanol and water to provide 1,7-bis-(1-methylethoxy)-2-naphthalenecarboxamide in 40% yield; mp 145°–146° C.

EXAMPLE 6

6-Methoxy-1-(1-methylethoxy)-2-naphthalenecarboxamide

To an ice water cooled solution of 6-methoxy-1-(1-methylethoxy)-2-naphthalenecarboxylic acid (5.0 g, 19 mmol) in 50 mL of THF is added 2 drops of DMF followed by oxalyl chloride (2.8 g, 21 mmol). The solution is stirred a room temperature for 2 hours then poured onto 150 mL of aqueous NH₄OH. An additional 700 mL of water is added and the resultant precipitate collected. Recrystallization from ethyl acetate provides 6-methoxy-1-(1-methylethoxy)-2-naphthalenecarboxamide in 74% yield; mp 183°–184° C.

EXAMPLE 7

1,7-Dimethoxy-2-naphthalenecarboximide

To a room temperature solution of 1,7-dimethoxy-2-naphthalenecarboxylic acid (131 mg, 0.56 mmol) in 3 mL of THF is added N,N-carbonyldiimidazole (105 mg, 0.65 mmol). The solution is heated at reflux for 2.5 hours and cooled slightly. Aqueous NH₄OH (1 mL) is added and the reaction mixture is stirred at room temperature for 1.5 hours, then poured into 1:1 hexane:ethyl acetate and washed with brine. The organic layer is dried over MgSO₄, filtered, and concentrated in vacuo. The crude product is chromatographed on silica gel eluting with hexane:ethyl acetate (1:1) to provide 1,7-dimethoxy-2-naphthalenecarboxamide in 49% yield; mp 134°–136° C.

We claim:

1. A compound of the formula

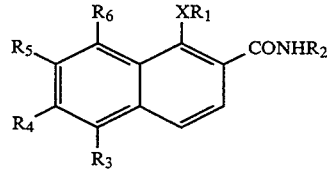

wherein
$R_1$ is lower alkyl, phenyl or benzyl;
$R_2$ is hydrogen or lower alkyl;
X is O; and
$R_3$, $R_4$, $R_5$ and $R_6$ are each independently hydrogen, hydroxy, halogen, trifluoromethyl, lower alkyl, lower alkoxy, phenoxy, benzyloxy, nitro, or —$NR_7R_8$ in which $R_7$ and $R_8$ are each independently hydrogen or lower alkyl, or a pharmaceutically acceptable acid addition salt thereof; with the proviso that either $R_4$ or $R_5$ must be lower alkoxy.

2. A compound of claim 1 wherein $R_3$ and $R_6$ are hydrogen.

3. A compound of claim 2 wherein $R_1$ is lower alkyl.

4. A compound of claim 1 and being 7-methoxy-1-(1-methylethoxy)-2-naphthalenecarboxamide.

5. A compound of claim 1 and being N-ethyl-7-methoxy-1-(1-methylethoxy)-2-naphthalenecarboxamide.

6. A compound of claim 1 and being 7-methoxy-1-(1-methylethoxy)-N-(1-methylethyl)-2-naphthalenecarboxamide.

7. A compound of claim 1 and being 1,7-bis-(1-methylethoxy)-2-naphthalenecarboxamide.

8. A compound of claim 1 and being 6-methoxy-1-(1-methylethoxy)-2-naphthalenecarboxamide.

9. A compound of claim 1 and being 1,7-dimethoxy-2-naphthalenecarboxamide.

10. A pharmaceutical composition comprising a therapeutically effective amount of a compound of claim 1 together with a pharmaceutically acceptable carrier.

11. A method of treating inflammatory diseases comprising administering to a host in need thereof a pharmaceutical composition of claim 10 in unit dosage form.

* * * * *